(12) United States Patent
Cappello

(10) Patent No.: US 7,445,783 B2
(45) Date of Patent: Nov. 4, 2008

(54) TOPICAL AND TRANSDERMAL TREATMENTS USING UREA FORMULATIONS

(75) Inventor: John V. Cappello, Myrtle Beach, SC (US)

(73) Assignee: Cappellos, Inc., King of Prussia, PA (US)

( * ) Notice: Subject to any disclaimer, the term of this patent is extended or adjusted under 35 U.S.C. 154(b) by 0 days.

(21) Appl. No.: 11/590,037

(22) Filed: Oct. 30, 2006

(65) Prior Publication Data

US 2008/0102089 A1     May 1, 2008

(51) Int. Cl.
*A61K 39/00*     (2006.01)
(52) U.S. Cl. .................................. 424/184.1
(58) Field of Classification Search ............... 424/184.1
See application file for complete search history.

(56) References Cited

U.S. PATENT DOCUMENTS

2005/0074461 A1*    4/2005    Donovan ................. 424/184.1

OTHER PUBLICATIONS

Arana et al (Am. J. Trop. Med. Hyg. vol. 65, No. 5, pp. 466-470, 2001).*

* cited by examiner

*Primary Examiner*—Mark Navarro
(74) *Attorney, Agent, or Firm*—Lawrence J. Shurupoff

(57) ABSTRACT

Various medical conditions previously treated by injection or surgery are effectively treated by a topical application of a composition of urea and a chemotherapeutic agent. Such agents include sclerosing agents, varodilators and botulinum toxin. Conditions as diverse as spider veins, erectile dysfunction and facial wrinkles can be effectively treated with the compositions.

4 Claims, No Drawings

TOPICAL AND TRANSDERMAL TREATMENTS USING UREA FORMULATIONS

BACKGROUND OF THE INVENTION

Field of the Invention

The present invention relates in general to compositions containing urea, and to methods of treating medical conditions using such compositions.

SUMMARY OF THE INVENTION

Urea, by nature of its keratolytic action and humectant effect appears to prepare the substrate of the skin for ideal topical penetration of chemotherapeutic agents, and particularly those agents described herein. This action is believed to be effective with other chemotherapeutic agents in a broader sense. The complete mechanism of action of these agents with urea is not fully understood. What is known is that other topical formulations tried without urea were not effective or as effective as those used in combination with urea in topically treating various medical conditions.

An effective urea concentration for its topical use in combination with other chemotherapeutic agents is believed to be in the range of 10% to 40% by weight of the formulation. One specific urea-containing formulation used was an over-the-counter topical skin cream sold under the brand Dermal Therapy and manufactured by Bayer. The Dermal Therapy formulation contains deionized water, urea USP, propylene glycol, triethanolamineamine, hydrogenated polyisobutene, isopropyl myristate, lactic acid, cetyl alcohol, GMS PEG stearate, malic acid, emulsifying wax, silk protein amino acid, idmadazolidinyl urea, carbamer 941, sorbic acid, tetra sodium EDTA, and quatemium 15.

This Dermal Therapy product formulation will be referred to herein as "the base" to which other chemotherapeutic agents are combined to form a topical therapeutic skin cream. Of course, other skin creams, lotions or oils containing urea can also be effectively used. It is only the urea in the Dermal Therapy base which is considered necessary to carry out the present invention. The ingredients other than urea in Dermal Therapy are not necessary to achieve the results described in detail below.

Other bases without urea have been tried without success. For example, petroleum jelly and other cosmetic creams without urea were tried to treat the conditions noted below without success. Only when urea was included in the formulation were any positive results achieved. Any suitable carrier for applying urea and a therapeutic agent to the skin can be used in accordance with the invention.

Various other objects, features and attendant advantages of the present invention will be more fully appreciated as the same becomes better understood from the following detailed description.

DETAILED DESCRIPTION

A particularly effective use of urea has been found in the topical treatment of spider veins and superficial varicosities. These are common skin problems occurring on the legs and on the face as telangectasias. As such, they are deemed unsightly in general by those who have them.

By mixing a sclerosing agent to the base (Dermal Therapy) in a formulation containing 1 to 10% by weight of such an agent, spider veins disappear or become progressively better (less visible) after 90 days of treatment. The formulation was used at least two times per day, at least once in the morning and at least once in the evening. The specific agent used was sodium morrhuate in an amount of 5% by weight. However, sodium morrhurate can be used effectively in the range of 1% to 10% by weight. By extension, other such sclerosing agents, or mixtures thereof, including ethyl morrhuate, Vitamin K, hypertonic saline, dextrose solution and any other known injectible sclerosing agents should also work effectively in such treatment, both topically and transdermally.

Three female patients with spider veins covering 1 to 3 square inches on their anterior thighs were topically administered 5% by weight of sodium morrhuate in the base. Within 90 days, all three patients were completely resolved of any spider vein appearances.

In other examples, formulations with 1 cc to 10 cc of sodium mourrhuate in a one ounce vanishing cream base (the base) were given to subjects to apply to their spider veins and small varicosites on a daily basis. In the half dozen subjects tested, the spider veins and small varicosities were eliminated. Results were obtained in 30 to 90 days, on average, and may vary based upon compliance of using the composition daily to the affected sites.

Another application of urea formulations is in the topical treatment of erectile dysfunction. There are two major physical causes of erectile dysfunction. One cause is a decrease in nitric oxide and the other is a decrease of circulation to the penis and corpus cavernous. If this circulation is hampered, the effect of exogenous or endogenous nitric oxide production will be diminished.

By mixing a vasodilator such as menthol or eucalyptol, or a mixture thereof, to the base in a formulation containing 0.04% to 1% by weight of such a vasodilator, or mixture of vasodilators, improved erections were obtained within 90 days without the addition of nitric oxide enhancing agents. The vasodilator formulation was used at least two times per day, morning and evening, and applied generously over the shaft of the penis.

Three males who had experienced erectile problems relating to the inability to enter the vagina in a hardened state reported gradual improvement to the stage of again being able to experience intravaginal orgasm. This improvement occurred over a 90 day period of application. It is likely that ongoing use of the treatment may be needed, since the salubrious effect of the topical composition does not appear to be a permanent one of blood vessel dilation.

By extension, other vasodilators such as propranolol, and others in its class of beta blockers as well as any known pharmaceutical which is known to produce vasodilation can be added to a base containing urea. This would also include the addition of calcium channel blockers and nitrates to the base.

The use of urea in combination with other topical agents has proved useful in the treatment of Peyronie's disease. This condition is a result of blood vessel plaquing in the penile shaft, as well as concomitant faulty blood circulation.

A formulation using 0.05% to 5.0% by weight of propranolol in the previously mentioned base (Dermal Therapy) was used on an individual with Peyronie's disease so severe as not to permit penile entry in the vagina. The specific formulation contained 0.5% propranolol. Within 90 days of using the formulation in the morning and at bedtime, the subject, with a downward "C" penile arc, gradually attained a straightened penis over 90 days, thereby permitting vaginal entry. Once again, it is believed that any known pharmaceutical with a vasodilation effect would produce similar results with the base.

Another application of urea base formulations is effective in treating facial wrinkles. Botox, (botulinum toxina) is known to produce an effect of decreasing wrinkles through muscle relaxation. However, until now, Botox only has worked by injection. Retin A produces a similar decrease in skin aging through a different mechanism over a longer period of time by causing desquamation, thereby permitting other topicals to enter the dermis. Retin A along with the base effectively permits entry of Botox into and through the skin.

The use of Botox, Retin A and the base creates a formulation capable of safely, and in a low dose, dramatically decreasing facial wrinkles around the eyes and mouth.

Formulations containing as low as 0.05% by weight of Botox and 0.05% by weight Retin A mixed within the base have been used successfully in 12 subjects. The wrinkle reducing effect occurs over a 72 hour period and lasts up to one week. Such a product is used for nighttime application over wrinkled areas on an as—needed basis. While higher concentrations may be considered, it is best to err on the side of least possible harm by using lower concentrations of Botox and Retin A.

The topical application of known pharmaceutical agents can cause an improvement in a medical condition. The use of the base containing urea USP augments and facilitates the medical improvement. Urea appreas to enhance and facilitate transport of chemotherapeutic agents through the skin.

Other variations are within the spirit of the present invention. Thus, while the invention is susceptible to various modifications and alternative constructions, certain embodiments thereof have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

What is claimed is:

1. A composition for the topical treatment of a medical condition, comprising:
    urea in an amount of 10% to 40% by weight;
    a chemotherapeutic agent comprising botulinum toxin in an amount effective to treat the medical condition; and
    tretinoin in an amount of at least 0.05% by weight.

2. A method of topically treating a medical condition, comprising:
    providing a composition comprising urea, a botulinum toxin and tretinoin; and
    applying said composition topically to a skin portion affected by said medical condition, such that said urea and said tretinoin facilitate entry of said botulinum toxin into said skin portion.

3. The method of claim 2, wherein said medical condition comprises facial winkles and said method further comprises applying said composition to said facial wrinkles.

4. A composition for the treatment of a medical condition, comprising:
    urea in an amount of 10% to 40% by weight;
    tretinoin in an amount of at least 0.05% by weight; and
    botulinum toxin in an amount of at least 0.05% by weight.

* * * * *